(12) United States Patent
Blanco et al.

(10) Patent No.: US 10,098,790 B2
(45) Date of Patent: Oct. 16, 2018

(54) ADHESIVE ARTICLES

(71) Applicant: Alfred E. Mann Institute for Biomedical Engineering at the University of Southern California, Los Angeles, CA (US)

(72) Inventors: Cesar Blanco, Los Angeles, CA (US); Jonathan Gregory Lasch, Calabasas, CA (US)

(73) Assignee: University of Southern California, Los Angeles, CA (US)

( * ) Notice: Subject to any disclaimer, the term of this patent is extended or adjusted under 35 U.S.C. 154(b) by 215 days.

(21) Appl. No.: 14/443,332

(22) PCT Filed: Dec. 9, 2013

(86) PCT No.: PCT/US2013/073922
§ 371 (c)(1),
(2) Date: May 15, 2015

(87) PCT Pub. No.: WO2014/093246
PCT Pub. Date: Jun. 19, 2014

(65) Prior Publication Data
US 2015/0297413 A1 Oct. 22, 2015

Related U.S. Application Data

(60) Provisional application No. 61/737,297, filed on Dec. 14, 2012.

(51) Int. Cl.
*A61F 13/02* (2006.01)
*A61L 24/06* (2006.01)
(Continued)

(52) U.S. Cl.
CPC ........ *A61F 13/025* (2013.01); *A61F 13/0253* (2013.01); *A61L 24/06* (2013.01);
(Continued)

(58) Field of Classification Search
CPC ...... A61F 13/00; A61F 13/02; A61F 13/0246; A61F 13/025; A61F 13/0253;
(Continued)

(56) References Cited

U.S. PATENT DOCUMENTS 5,585,178 A * 12/1996 Calhoun ............... B32B 7/12
428/343
6,242,665 B1 * 6/2001 Malowaniec ....... A61F 13/0203
602/41
(Continued)

FOREIGN PATENT DOCUMENTS

| CN | 1348971 A | 5/2002 |
|---|---|---|
| CN | 1930204 A | 3/2007 |
| CN | 101304712 A | 11/2008 |

OTHER PUBLICATIONS

European Patent Office (EPO). 2016. Communication Pursuant to Article 94(3) EPC, dated Nov. 7, 2016, for European Application EP 13 86 2696, entitled "Adhesive Articles," European regional phase of PCT/US2013/073922, of which the instant application is a US national phase application.
(Continued)

*Primary Examiner* — Keri J Nelson
(74) *Attorney, Agent, or Firm* — McDermott Will & Emery LLP

(57) ABSTRACT

This disclosure relates generally to adhesive articles and particularly to adhesive articles comprising a reversible adhesive layer and a non-reversible adhesive layer. The adhesive article may further comprise a backing material. The adhesive article may further comprise a dressing material. Such adhesive articles may be particularly suitable for treatment of damaged sensitive tissue, for example wounds formed on a fragile skin.

12 Claims, 7 Drawing Sheets

(51) Int. Cl.
  *C09J 133/06* (2006.01)
  *C09J 133/26* (2006.01)
  *C09J 7/20* (2018.01)
  *C09J 7/00* (2018.01)

(52) U.S. Cl.
  CPC . *C09J 7/00* (2013.01); *C09J 7/20* (2018.01); *C09J 133/06* (2013.01); *C09J 133/26* (2013.01); *C09J 2201/40* (2013.01); *C09J 2201/61* (2013.01); *C09J 2433/00* (2013.01); *C09J 2477/00* (2013.01)

(58) Field of Classification Search
  CPC ........ A61F 13/0256; A61F 2013/00089; A61F 2013/00655; A61F 2013/00659; A61F 2013/00663; A61F 2013/00668; A61F 2013/00672; A61F 2013/00685; A61L 24/00
  USPC .................. 602/41, 42, 54, 55; 523/105, 111
  See application file for complete search history.

(56) References Cited

U.S. PATENT DOCUMENTS

| | | |
|---|---|---|
| 2003/0031861 A1 | 2/2003 | Reiter |
| 2005/0013957 A1 | 1/2005 | Leschinsky |
| 2005/0037194 A1 | 2/2005 | Green et al. |
| 2009/0145550 A1 | 6/2009 | Dellevigne |
| 2009/0216170 A1 | 8/2009 | Robinson et al. |
| 2012/0109035 A1 | 5/2012 | Zhang et al. |

OTHER PUBLICATIONS

Mi, L. et al. 2011. A Thermoresponsive Antimicrobial Wound Dressing Hydrogel Based on a Cationic Betaine Ester. Adv. Funct. Mater. 2011, vol. 21, pp. 4028-4034.

ISA/KR. 2014. International Search Report and Written Opinion of the International Searching Authority, dated Mar. 25, 2014, for PCT Application PCT/US2013/073922, entitled "Adhesive Articles," filed Dec. 9, 2013.

European Patent Office (EPO). 2016. Extended European Search Report (EESR), dated May 23, 2016, for European Application EP 13 86 2696, entitled "Adhesive Articles," European regional phase of PCT/US2013/073922, of which the instant application is a US national phase application.

European Office Action from European Application No. 13862696.5, dated Jul. 7, 2017, 5 pages.

European Office Action from European Application No. 13862696.5, dated Mar. 17, 2017.

Chinese Office Action from Chinese Application No. 201380064958.0, dated Dec. 5, 2017, 18 pages.

* cited by examiner

ADHESIVE ARTICLES

CROSS-REFERENCE TO RELATED APPLICATIONS

This application is based upon and claims priority to U.S. Provisional Application No. 61/737,297, filed Dec. 14, 2012, entitled "Adhesive Articles," the entire content of which is incorporated herein by reference.

TECHNICAL FIELD

This disclosure relates generally to adhesive articles. This disclosure further relates to adhesive articles comprising a reversible adhesive layer and a non-reversible adhesive layer.

BACKGROUND

Adhesive articles incorporating pressure-sensitive adhesives are well known and commercially available. Examples of adhesive articles are medical dressings such as adhesive bandages, transdermal drug patches and surgical patches.

Although such adhesives immediately adhere to a surface when pressure is applied, their removal from the surface becomes a hurdle later. For example, a bandage manufactured by using a pressure-sensitive adhesive can easily be applied to a wound formed on a skin with high adherence. However, when this bandage is to be removed from the skin to replace it with another bandage or after completion of treatment of the wound, a force needs to be applied to counteract high adherence of the bandage, which may cause pain to the patient and/or damage to the wound or to the healthy tissue surrounding the wound. Such hurdles are very frequently encountered during interventions to wounds by trained personnel at medical institutions as well as individuals at home.

Furthermore, commercially available adhesive articles applied to fragile skins, such as those of newborn and geriatric populations, may not have adequate adhesion, may be easily displaced or inadvertently removed. Or, after such adhesive articles are applied, their removal may be difficult which may sometimes damage the underlying tissues. They may also not work well in humid environments.

Adhesive articles comprising thermally reversible adhesives have been disclosed, for example, in: Zhang et al. "Reversible Adhesives," U.S. Patent Publication No. 2012/0109035; Chen et al. "Preparation of Easily Stripped off Temporary Wound Dressing Materials by Radiation Grafting; Kubota "Wound Dressing", U.S. Patent Publication No. 2002/0028232. The entire content of these publications is incorporated herein by reference.

SUMMARY

This disclosure relates generally to adhesive articles. This disclosure further relates to adhesive articles comprising reversible adhesives.

The adhesive article may comprise at least one reversible adhesive layer and at least one non-reversible adhesive layer.

The reversible adhesive layer may comprise a reversible adhesive. The reversible adhesive may comprise a reversible polymer. The reversible polymer may be formed by reacting a formulation comprising a monomer of a reversible polymer. An example of the reversible adhesive layer may be a thermally reversible adhesive layer.

The non-reversible adhesive layer may not have the reversibility of the reversible adhesive layer. The non-reversible adhesive layer may comprise a non-reversible adhesive. The non-reversible adhesive layer does not contain any reversible adhesive. That is, the non-reversible adhesive layer is free of the reversible adhesive.

The adhesive article may further comprise at least one frontal surface. The at least one reversible adhesive layer may be on the at least one frontal surface. The at least one non-reversible adhesive layer may be on the at least one frontal surface. The at least one reversible adhesive layer may be deposited on the at least one frontal surface. The at least one non-reversible adhesive layer may be deposited on the at least one frontal surface.

The at least one reversible adhesive layer may cover at least 0.1 percent surface area of the at least one frontal surface. The at least one non-reversible adhesive layer may cover at least 0.1 percent surface area of the at least one frontal surface.

The at least one reversible adhesive layer may not be in contact with the at least one non-reversible adhesive layer. The at least one reversible adhesive layer may be in contact with the at least one non-reversible adhesive layer. The at least one reversible adhesive layer and the at least one non-reversible layer may overlap. The at least one reversible adhesive layer may cover part of the at least one non-reversible adhesive layer. The at least one non-reversible adhesive layer may cover part of the at least one reversible adhesive layer.

The at least one reversible adhesive layer may be deposited on the at least one frontal surface after the at least one non-reversible adhesive layer is deposited on the at least one frontal surface. The at least one reversible adhesive layer may be deposited on the at least one frontal surface before the at least one non-reversible adhesive layer is deposited on the at least one frontal surface.

The at least one reversible adhesive layer may have an adhesive strength higher than that of the at least one non-reversible adhesive layer. The at least one reversible adhesive layer may have an adhesive strength lower than that of the at least one non-reversible adhesive layer. The at least one reversible adhesive layer may have an adhesive strength higher than 0.1 N/cm$^2$ at a temperature above 20° C. The at least one reversible adhesive layer may have an adhesive strength lower than 0.1 N/cm$^2$ at a temperature above 20° C. The at least one non-reversible adhesive layer may have an adhesive strength higher than 0.1 N/cm$^2$ at a temperature above 20° C.

The adhesive article may further comprise at least one backing material. The at least one backing material may have at least one frontal surface. The at least one reversible adhesive layer may be on the at least one frontal surface of the backing material. The at least one reversible adhesive layer may be deposited on the at least one frontal surface of the backing material. The at least one reversible adhesive layer may cover at least 0.1 percent surface area of the at least one frontal surface of the backing material. The at least one non-reversible adhesive layer may be on the at least one frontal surface of the backing material. The at least one non-reversible adhesive layer may be deposited on the at least one frontal surface of the backing material. The at least one non-reversible adhesive layer may cover at least 0.1 percent surface area of the at least one frontal surface of the backing material.

The adhesive article may be an adhesive article that adheres to a human tissue. The tissue may be a skin. The skin may be a fragile skin. The fragile skin may be a fragile skin of a human belonging to a pediatric population. The fragile skin may be a fragile skin of a human belonging to a geriatric population.

The at least one reversible adhesive layer may be a thermally reversible adhesive layer.

The at least one reversible adhesive layer may comprise a reversible polymer. The reversible polymer may be formed by reacting a formulation comprising a monomer of a reversible polymer. The at least one reversible adhesive layer may comprise poly(N-isopropylacrylamide). The at least one non-reversible adhesive layer may be free of poly(N-isopropylacrylamide).

The adhesive article may be a wound dressing. This adhesive article may further comprise a wound dressing material. This adhesive article may be an adhesive article that adheres to a human tissue. This tissue may be a skin. This skin may be a fragile skin. This fragile skin may be a fragile skin of a human belonging to a pediatric population. This fragile skin may be a fragile skin of a human belonging to a geriatric population.

A method may comprise applying the adhesive article to a wound or a skin lesion. The wound may be a wound of a human skin. This human skin may be a fragile skin. This fragile skin may be a fragile skin of a human belonging to a pediatric population or a geriatric population.

Any combination of embodiments or examples disclosed above that comprise the reversible adhesive and the non-reversible adhesive may be suitable to form the adhesive article of this disclosure These, as well as other components, steps, features, objects, benefits, and advantages, will now become clear from a review of the following detailed description of illustrative embodiments, the accompanying drawings, and the claims.

BRIEF DESCRIPTION OF THE DRAWINGS

In the accompanying drawings, aspects of the adhesive articles are illustrated by way of example, and not by way of limitation. Thus, the drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

DETAILED DESCRIPTION OF ILLUSTRATIVE EMBODIMENTS

Figure 1:
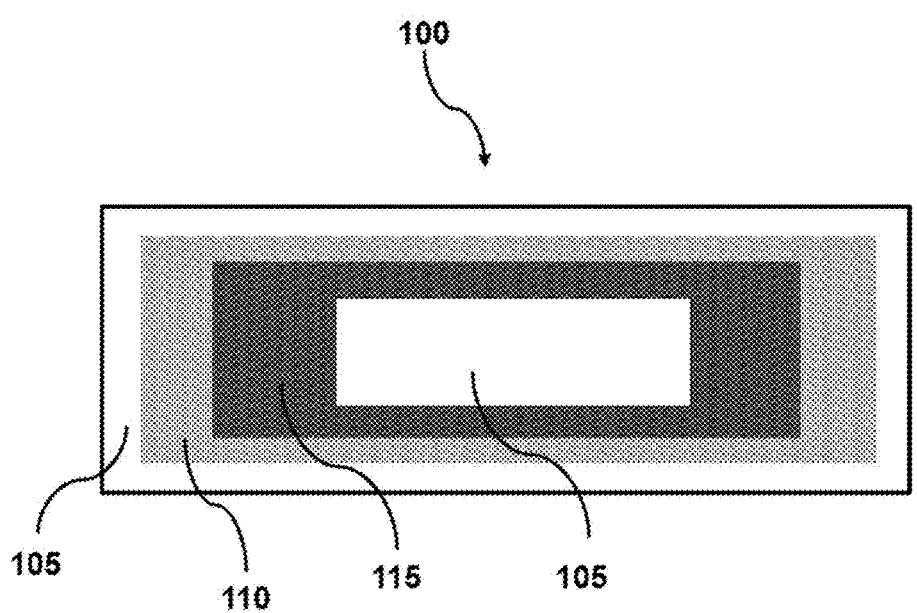
FIG. 1 is a frontal view of an exemplary adhesive article.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

This disclosure relates generally to articles comprising adhesives and particularly to articles comprising reversible adhesives. This disclosure further relates to an adhesive article comprising at least one reversible adhesive and at least one non-reversible adhesive.

The adhesive article may comprise at least one layer comprising a reversible adhesive, and at least one layer comprising a non-reversible adhesive.

The adhesive article may comprise at least one surface that may adhere to a tissue. This surface is called "the frontal surface" hereafter. When the adhesive article is applied to the tissue, the frontal surface may be brought in contact with the tissue. The reversible adhesive layer may be on the frontal surface. The non-reversible adhesive layer may be on the frontal surface. The reversible adhesive and the non-reversible adhesive may be deposited at least on the frontal surface and each form a layer on it. When the adhesive article is applied to the tissue, the at least one reversible adhesive layer and/or the at least one non-reversible adhesive layer may be brought in contact with the tissue.

The reversible adhesive layer may have a surface that adheres to the tissue when the adhesive article is brought in contact with the tissue. Similarly, the non-reversible adhesive layer may have a surface that adheres to the tissue when the adhesive article is brought in contact with the tissue.

The reversible adhesive layer may cover at least 0.1 percent, 1 percent, 10 percent, or substantially the entire frontal surface. The non-reversible adhesive layer may cover at least 0.1 percent, 1 percent, 10 percent, or substantially the entire frontal surface.

The reversible adhesive may have any thickness. For example, the reversible adhesive layer may have a thickness equivalent to the characteristic molecular length of a chemical compound that forms the reversible adhesive layer. Or, the reversible adhesive layer may be at least 10 nm, at least 100 nm, at least 1000 nm, at least 1 micrometer, at least 10 micrometers or at least 100 micrometers thick. Or, the thickness of the reversible adhesive layer may vary in the range of 1 nm to 1,000 micrometers, 10 nm to 100 micrometers, or 100 nm to 10 micrometers. This thickness of the reversible adhesive may form at least one side surface of the reversible adhesive.

Similarly, the non-reversible adhesive may have any thickness. For example, the non-reversible adhesive layer may have a thickness of a chemical compound that forms the reversible adhesive layer. Or, the non-reversible adhesive layer may be 10 nm, 100 nm, 1000 nm, 1 micrometer, 10 micrometers or 100 micrometers thick. Or, the thickness of the non-reversible adhesive layer may vary in the range of 1 nm to 1,000 micrometers, 10 nm to 100 micrometers, or 100 nm to 10 micrometers. This thickness of the non-reversible adhesive may form at least one side surface of the non-reversible adhesive layer.

The reversible adhesive layer may be in contact with (i.e. may touch) the non-reversible adhesive layer. For example, the side surface of the reversible adhesive layer may be partially or substantially in contact with the non-reversible adhesive layer. Or, the reversible adhesive layer and the non-reversible adhesive layer may overlap. For example, the reversible adhesive layer may partially or substantially cover the non-reversible adhesive layer. Or, the non-reversible adhesive layer may partially or substantially cover the reversible adhesive layer. The overlapping area may be in the range of 1% to 99%, 10% to 90%, 20% to 80% or 30% to 70% of the frontal surface area of the reversible adhesive layer.

Also, the reversible adhesive layer may not be in contact with the non-reversible adhesive layer. Furthermore, the frontal surface may have a surface free of both the reversible adhesive layer and the non-reversible adhesive layer.

The reversible adhesive layer may be deposited on the frontal surface after the deposition of the non-reversible adhesive layer. When deposited as such, the reversible adhesive layer may partially cover surface of the non-reversible adhesive layer. This partial coverage may be at least 0.1 percent, at least 1 percent, at least 10 percent, or substantially entire surface of the non-reversible adhesive layer.

The non-reversible adhesive layer may be deposited on the frontal surface after the deposition of the reversible adhesive layer. When deposited as such, the non-reversible adhesive layer may partially cover surface of the reversible adhesive layer. This partial coverage may be at least 0.1 percent, at least 1 percent, at least 10 percent, or substantially entire surface of the reversible adhesive layer.

The reversible adhesive layer may be on any surface of the adhesive article. The non-reversible adhesive layer may be on any surface of the adhesive article. For example, a double-sided tape may be formed by depositing the reversible adhesive layer on one side of the double-sided tape and the non-reversible adhesive layer on other side of the double-sided tape. In another example, both sides of the double-sided tape may comprise the reversible adhesive layer and the non-reversible adhesive layer.

The reversible adhesive layer may have an adhesive strength higher than that of the non-reversible adhesive layer. The reversible adhesive layer may have an adhesive strength lower than that of the non-reversible adhesive layer. Adhesive strength of the reversible adhesive may be higher than $0.01$ $N/cm^2$, $0.1$; $N/cm^2$, $1$ $N/cm^2$, or $5$ $N/cm^2$ at a temperature above $20°$ C. Adhesive strength of the reversible adhesive may be lower than $0.01$ $N/cm^2$, $0.1$ $N/cm^2$, or $1$ $N/cm^2$ at a temperature below $20°$ C.

Adhesive strength of the non-reversible adhesive may be higher than $0.01$ $N/cm^2$, $0.1$ $N/cm^2$, $1$ $N/cm^2$, or $5$ $N/cm^2$ at a temperature above $20°$ C.

The adhesive article may further comprise at least one backing material. The at least one backing material may comprises at least one frontal surface. The reversible adhesive layer and/or the non-adhesive layer may be on the frontal surface formed by the backing material. The reversible adhesive layer may cover at least 0.1 percent, 1 percent, 10 percent, or substantially the entire frontal surface of the backing material. The non-reversible adhesive layer may cover at least 0.1 percent, 1 percent, 10 percent, or substantially the entire frontal surface of the backing material. The reversible adhesive layer may be in contact with the non-reversible adhesive layer. The reversible adhesive layer and the non-reversible adhesive layer may overlap. Or, the reversible adhesive layer may not be in contact with the non-reversible adhesive layer. Furthermore, the frontal surface of the backing material may have a surface free of both the reversible adhesive layer and the non-reversible adhesive layer. The reversible adhesive layer may be deposited on the frontal surface of the backing material after the deposition of the non-reversible adhesive layer. When deposited as such, the reversible adhesive layer may partially cover surface of the non-reversible adhesive layer. This partial coverage may be at least 0.1 percent, 1 percent, 10 percent, or substantially entire surface of the non-reversible adhesive layer. The non-reversible adhesive layer may be deposited on the frontal surface of the backing material after the deposition of the reversible adhesive layer. When deposited as such, the non-reversible adhesive layer may partially cover surface of the reversible adhesive layer. This partial coverage may be at least 0.1 percent, 1 percent, 10 percent, or substantially entire surface of the reversible adhesive layer.

The adhesive article may also be free of any backing material. For example, the adhesive article may consist of the reversible adhesive layer and the non-reversible adhesively layer. In another example, the adhesive article may consist of the reversible adhesive layer, the non-reversible adhesive layer and adhesive-free volume formed by the reversible adhesive layer and the non-reversible adhesive layer.

The adhesive article may also further comprise at least one dressing material. The dressing material may be on at least on the frontal face. When the adhesive article is applied, the dressing material may be brought in contact with the tissue.

The tissue may be any organic tissue comprising an aggregate of cells. For example, the tissue may be any tissue of an animal. The tissue may also be any tissue of a mammal. The mammal may be a human. The tissue may comprise a tissue that may be healthy or in a normal condition. The tissue may further comprise a tissue that may be unhealthy or not in a normal condition.

An example of such unhealthy tissue may be a wound. Another example of such unhealthy tissue may be a skin lesion. Examples of skin lesions may include skin diseases, conditions, injuries, defects, abnormalities or combinations thereof. An example of such skin lesion may be common warts, precancerous lesions (such as actinic keratosis), immune-related conditions (such as psoriasis) or combinations thereof.

Another example of the tissue is a fragile skin. One example of fragile skin is a sensitive skin of a human belonging to a pediatric population. An example of such a human is a newborn baby. Another example of the fragile skin is a sensitive skin of a human belonging to a geriatric population.

Age-related changes in skin morphology in the elderly results in the development of fragile skin. With age, the outer skin layer (epidermis) becomes thinner, with decreases in extracellular components, such as collagen and elastin, which leads to decreases in tensile strength and elasticity of the skin. Other age-related skin changes include thinning of the subcutaneous fat layer, increased blood vessel fragility and a decrease in the adhesiveness between the dermis and the underlying loose connective tissues, resulting in increased vulnerability to skin tears and ruptures. Fragile skin can also be induced by cancer chemo- and radiation therapy. Humans with fragile skin are prone to have wounds caused by strains inflicted on such skins at levels negligible to normal human skin. For example, a soft impact on a fragile skin by an object can easily induce a wound on a fragile skin. If such a wound is covered with a commercially available typical wound dressing (e.g., an adhesive bandage) for protective or treatment purposes, the removal of the wound dressing later becomes an important problem due to considerable adherence of the wound dressing to the fragile skin. Removal of this typical wound dressing can easily cause further damage to the fragile skin or to the wound formed on such skin.

The adhesive article comprising the reversible adhesive layer and the non-reversible adhesive layer may provide a solution for this important problem. With the reversible adhesive layer, it may be easier to remove the adhesive article from the tissue after the adhesive article is applied. For example, the reversible adhesive layer surface of the adhesive article may adhere to the fragile skin at skin temperature and may easily be removed with minimal force and negligible or no further damage to the fragile skin when the adhesive article is cooled below the skin temperature, for example by using cold air, cooled compresses or ice. Thus, presence of the reversible adhesive layer may reduce the adhesiveness of the adhesive article at a lowered temperature and thereby aid its removal with minimal damage or pain to the fragile skin. The non-reversible layer may provide additional adhesive strength to the adhesive article and prevent accidental displacement or unintentional removal of the adhesive article from the fragile tissue.

The tissue may also be a tissue of a non-human organism such as another mammal, vertebrate or microorganism. The tissue may even be a living or dead cell culture. The tissue may be in any condition, e.g., it can be wet or dry.

Also, the adhesive article may be suitable for any non-tissue surface. For example, the adhesive article may be suitable in binding a wood surface to a glass surface. In another example, the adhesive article may be suitable in binding a medical instrument to any inorganic surface such as cloth or plastic.

The adhesive article may also be suitable in binding any two surfaces together, for example in binding the wound dressing to a wounded skin.

A method may comprise applying the adhesive article to a wound or a skin lesion. The wound may be a wound of a human skin. This human skin may be a fragile skin. The fragile skin may be a fragile skin of a human belonging to a pediatric population or a geriatric population.

The invention is illustrated further by the following additional examples that are not to be construed as limiting the invention in scope to the specific procedures or products described in them.

Examples of the Adhesive Article

As shown in FIG. 1, an exemplary adhesive article 100 may comprise at least one backing material 105, at least one non-reversible adhesive layer 110, and at least one reversible adhesive layer 115. In this example, the at least one non-reversible adhesive layer 110 and the at least one reversible adhesive layer 115 are in contact with each other.

Figure 2:
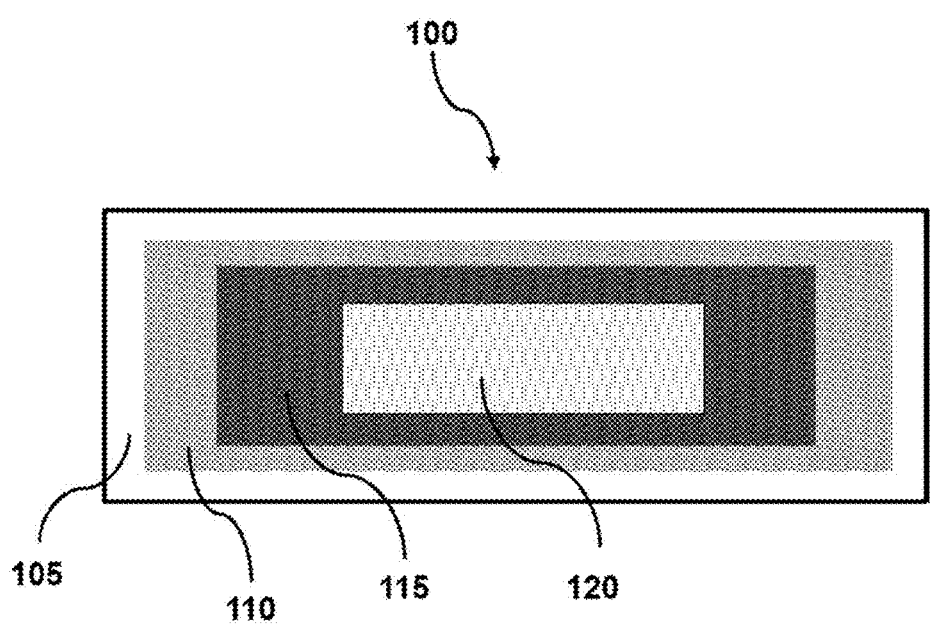
FIG. 2 is a frontal view of an exemplary adhesive article.

In another example, an exemplary adhesive article may further comprise at least one dressing material 120, as shown in FIG. 2.

Figure 3:
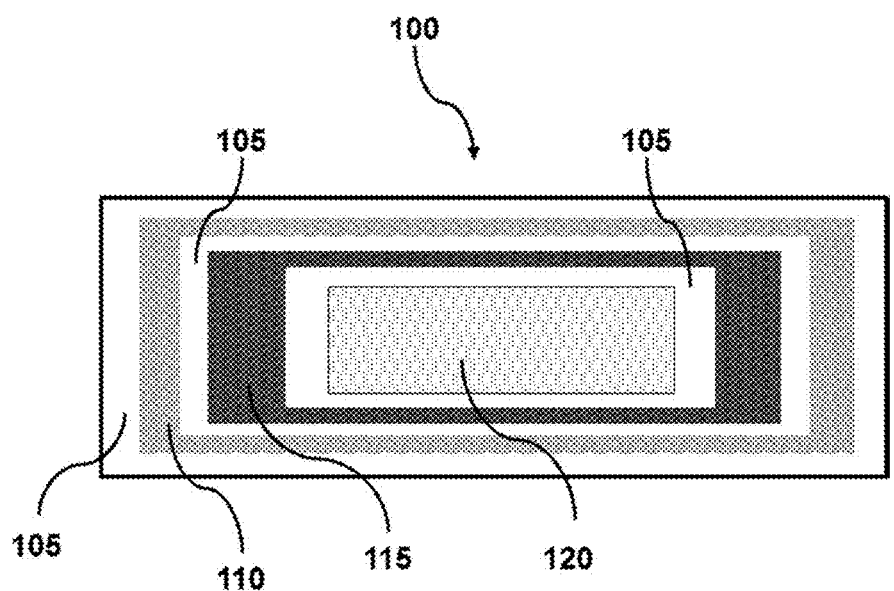
FIG. 3 is a frontal view of an exemplary adhesive article.
Figure 6:
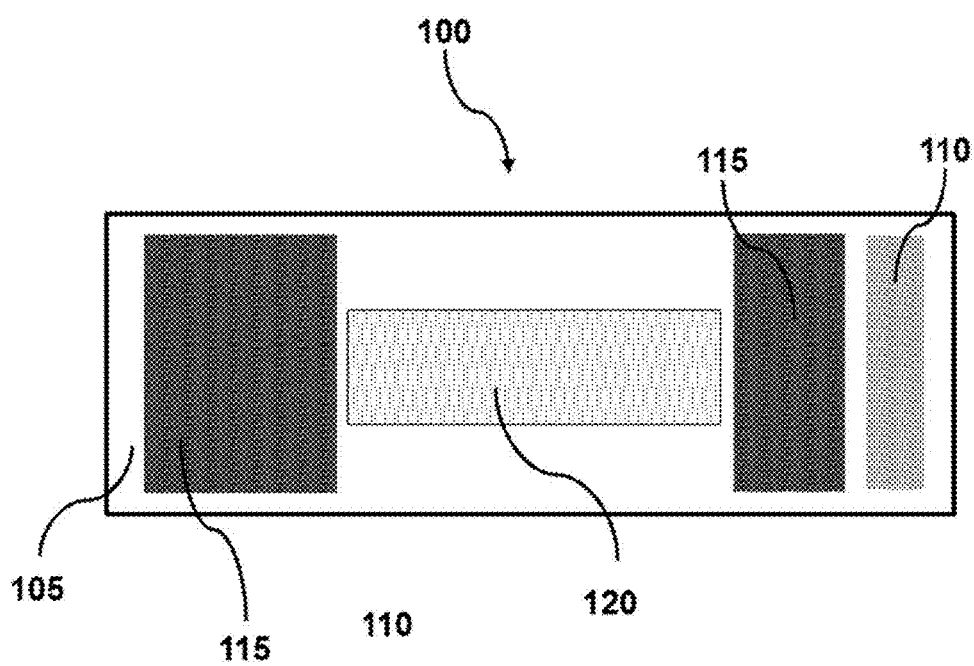
FIG. 6 is a frontal view of an exemplary adhesive article.
Figure 7:
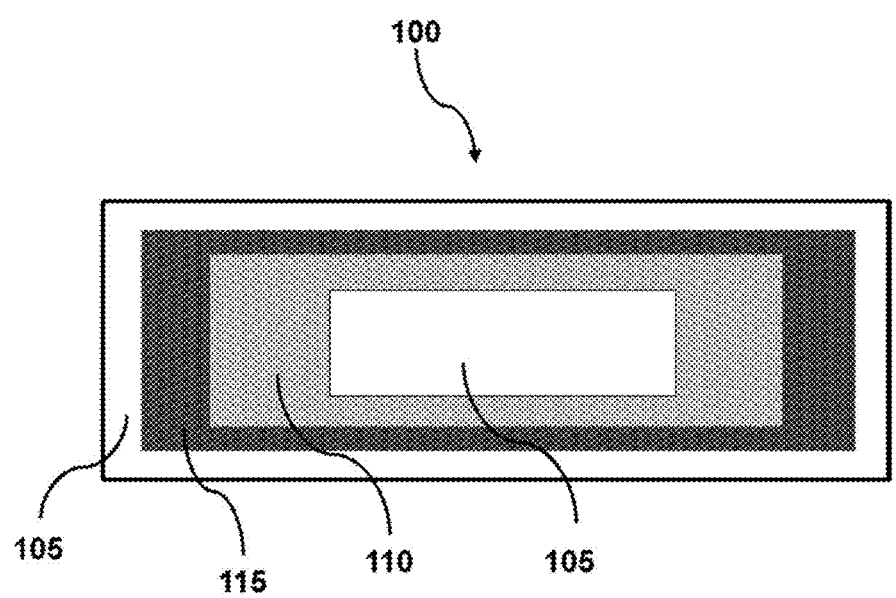
FIG. 7 is a frontal view of an exemplary adhesive article.

The reversible adhesive layer 115 and the non-reversible adhesive layer 110 may be in contact with each other, as shown in FIGS. 1-2 and 7. These layers may also overlap each other (not shown in the figures). These layers also may not be in contact with each other, as shown in FIGS. 3-6. The non-reversible adhesive layer 110 may surround the reversible adhesive layer 115, as shown in FIGS. 1-3. The reversible adhesive layer 115 may also surround the non-reversible adhesive layer 110, as shown in FIG. 7.

Figure 4:
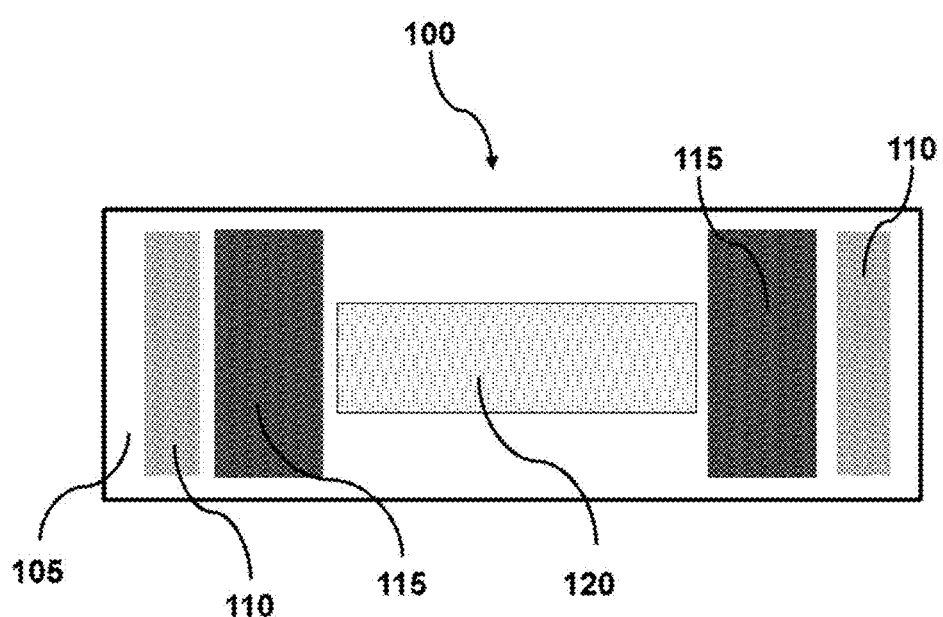
FIG. 4 is a frontal view of an exemplary adhesive article.
Figure 5:
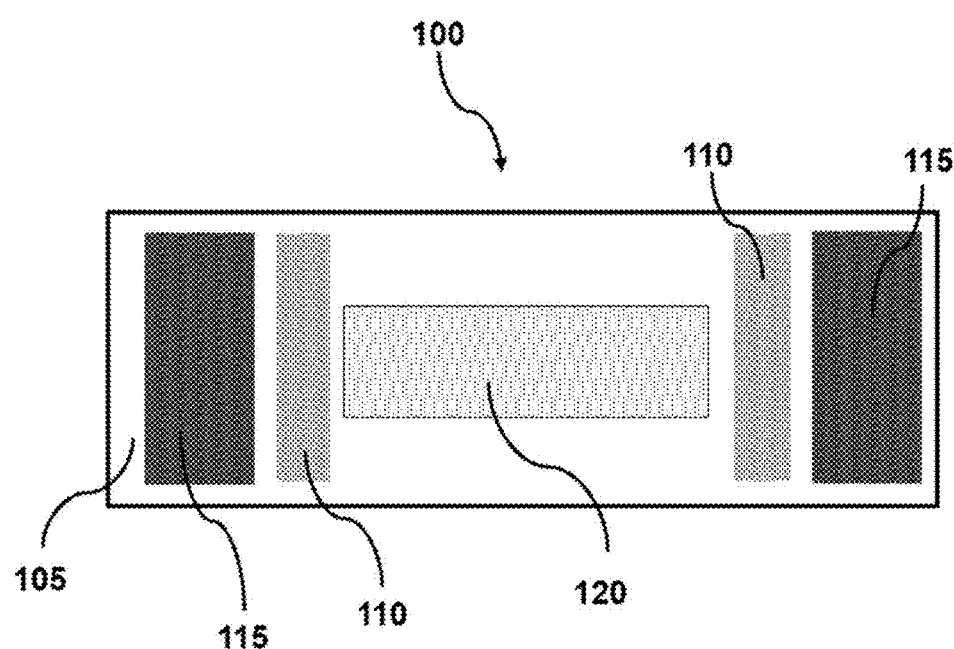
FIG. 5 is a frontal view of an exemplary adhesive article.

The reversible adhesive layer 115 and the non-reversible adhesive layer 110 may each be deposited on the frontal surface of the adhesive article in the form of segments, as shown in FIGS. 4-6.

The frontal surface of the adhesive article may have a region that is free of the reversible adhesive layer 115 and the non-reversible adhesive layer 110, as shown in FIGS. 1-6. (This region is not numbered in the figures.)

Examples of the Reversible Adhesive Layer

The reversible adhesive layer may comprise the reversible adhesive. For example, the reversible adhesive layer may be formed by deposition of a formulation comprising the reversible adhesive on the frontal surface of the adhesive article.

The reversible adhesive layer may be an adhesive that may have better adhesive properties or higher adhesiveness at a first predetermined condition than at a second predetermined condition. For example, the reversible adhesive layer may provide sufficient adhesiveness at or above a skin temperature such that the adhesive article incorporating such a reversible adhesive layer properly adheres to the tissue, for example at about 37° C. (i.e. the first predetermined condition). When this adhesive article is cooled below 37° C. (i.e. the second predetermined condition), for example by using ice, the adhesiveness of the reversible adhesive layer may thereby be substantially reduced to a level that the adhesive article can be removed from the tissue with reduced or negligible force and minimal damage to the tissue. That is, adhesiveness of this thermally reversible adhesive layer at about 37° C. may substantially be higher than its adhesiveness below 37° C. In this example, the reversible adhesive layer may be thermally reversible at about 37° C. However, depending on the type of its application, the reversible adhesive layer may be thermally reversible at any other temperature.

This reversibility is desired: it can be turned on or off at will making it suitable for a wide variety of applications where reversibility of adhesiveness is desired or even required.

The thermal reversibility is not the only mechanism by which the reversible adhesive layers can be manufactured. The reversibility of such layers can also be controlled by using other mechanisms. For example, such layers may provide sufficient adherence to a surface at normal lighting conditions (e.g. sun or artificial lights). But, their adhesiveness may be reduced to a negligible level when they are irradiated by an ultraviolet (UV) light. In another example, they may provide sufficient adhesiveness to tissue at normal humidity conditions (e.g., skin humidity or weather humidity). However, they may lose their adhesiveness when sufficient amount of solvent (e.g., water, alcohol and the like) is applied. All such reversible adhesive layers may be used. Such an adhesive layer is called the "reversible adhesive layer" in this disclosure.

The reversible adhesive layer may be suitable in binding any two surfaces together, for example in binding the adhesive article to the tissue. The tissue may be a human tissue or a tissue of a non-human organism such as another mammal, vertebrate or microorganism. The tissue may even be a living or dead cell culture. The tissue may be in any condition, e.g., it may be wet or dry.

The reversible adhesive layer may be suitable in binding any two non-tissue surfaces together. For example, the reversible adhesive layer may be suitable in binding a wood surface to a glass surface.

The reversible adhesive layer may comprise a reversible adhesive. The reversible adhesive may comprise a reversible polymer. For example, the reversible adhesive may be formed by reacting a formulation comprising a monomer of the reversible polymer. In another example, reacting a monomer of a thermally reversible polymer may form the reversible adhesive.

Thermally reversible polymers used to prepare the reversible adhesives have novel thermal behavior in aqueous media: they have inverse solubility with increasing temperature. Their molecular structure transition from a hydrophilic to a hydrophobic structure by heating, causing them to precipitate at a higher temperature while they are completely soluble at a lower temperature. This structural change may happen rather abruptly at a temperature what is known as the lower critical solution temperature (LOST). For example, while poly(N-isopropylacrylamide) is hydrophilic and completely soluble at a temperature below LOST, it becomes hydrophobic above LOST and precipitates out of an aqueous media. For this thermally reversible polymer, LOST is in the range of 30° C. to 35° C. This polymer is adhesive to the tissue above LOST and has substantially lowered or even negligible adhesiveness below LOST.

There are many reversible polymers that can be used to prepare the reversible adhesives. Their LOST may change together with their molecular structure. Copolymers of a thermally reversible polymer with other thermally reversible polymer or any other polymer can also be prepared to obtain polymers with varying LCSTs. Thereby, LOST may be controlled at a desired level by having variety of homopolymers and copolymers and numerous reversible adhesives may be obtained for wide variety of medical or non-medical applications. All such homopolymers and copolymers are within the scope of this invention.

In one embodiment, the thermally reversible polymer is thermally reversible at a temperature within the range of 0° C. to 100° C. In another embodiment, the thermally reversible polymer is thermally reversible at a temperature within the range of 0° C. to 50° C.

Examples of thermally reversible polymers and their typical LCSTs are poly(N-methyl-N-n-propylacrylamide), about 19.8° C.; poly(N-n-propylacrylamide), about 21.5° C.; poly(N-methyl-N-isopropylacrylamide) about 22.3° C.; poly(N-n-propylmethacrylamide), about 28.0° C.; poly(N-isopropylacrylamide), about 30.9°; poly(N, n-diethylacrylamide), about 32.0° C.; poly(N-isopropylmethacrylamide), about 44.0° C.; poly(N-cyclopropylacrylamide), about 45.5° C.; poly(N-ethylmethyacrylamide), about 50.0° C.; poly(N-methyl-N-ethylacrylamide), about 56.0° C.; poly(N-cyclopropylmethacrylamide), about 59.0° C.; and poly(N-ethylacrylamide), about 72.0° C., and their co-polymers with other polymers, and mixtures thereof. Another example of a thermally reversible polymer is acrylate-modified tri-block copolymer of polyethylene oxide (PEO)-co-poly(p-phenylene oxide) (PPO)-co-polyethylene glycol (PEO). In the last example, the molecular ratio of each polymer can be varied to vary the LOST of the polymer. Examples of thermally reversible monomers that can be used for the purposes of the instant invention are the monomers used in preparation of such thermally reversible polymers.

The thermally reversible polymers may be polymers prepared by polymerization of monomers of N-alkylacrylamide, N-alkylmethacrylamide or mixtures thereof. One example of such a monomer is N-isopropylacrylamide. And one example of such a polymer is poly(N-isopropylacrylamide).

The reversible adhesive may further comprise a conventional adhesive such as a pressure-sensitive adhesive or a chemical compound used in manufacturing such conventional adhesive. The conventional adhesive or the chemical compound used in manufacturing the conventional adhesive may improve the adhesive strength of the reversible adhesive. However, the adhesiveness of the reversible adhesive is controlled or turned on or off by incorporation of the reversible adhesives or chemical compounds used in manufacturing of such reversible adhesives to chemical structure or formulation of the conventional adhesives.

Examples of conventional adhesives are polymers of pressure-sensitive adhesives such as acrylate and/or methacrylate polymers formed by polymerization of acrylate monomers. Examples of such acrylate monomers are acrylic acid, methyl acrylate, methyl methacrylate, ethylacrylate, ethyl methacrylate, propyl acrylate, propyl methacrylate, n-butyl acrylate, n-butyl methacrylate, n-pentyl acrylate, n-hexyl acrylate, n-hexyl methacrylate, n-heptyl acrylate, n-octyl acrylate, n-nonyl acrylate, lauryl acrylate, stearyl acrylate, stearyl methacrylate, behenyl acrylate, octadecylacrylate, 2-ethylhexyl acrylate and mixtures thereof.

The reversible adhesive layer may have any thickness, but the thickness is at least equal to or thicker than that of the chemical compound forming the layer. For example, if the layer comprises N-isopropylacrylamide monomer, its thickness is equal to or thicker than that of this monomer. Sizes of dimers, trimers, oligomers or polymers of varying molecular weight of such monomers can also form the thickness of each individual layer.

If the layer is thinner than a predetermined thickness, the reversible adhesive layer may not have the desired properties. For example, if the thickness of the layer deposited by using a thermally reversible monomer is too thin, the reversible adhesive layer may not have sufficient adhesiveness. The predetermined thickness range may depend on the chemical or physical properties of the chemical compound forming the reversible adhesive layer and its value may vary accordingly. This thickness may experimentally be determined for the reversible adhesive layer.

One example of a reversible adhesive is disclosed in Zhang et al. "Reversible Adhesives", U.S. Patent Publication No. 2012/0109035. The entire content of this publication is incorporated herein by reference.

The reversible adhesive layer may have an adhesive strength higher than that of the non-reversible adhesive layer. The reversible adhesive layer may have an adhesive strength lower than that of the non-reversible adhesive layer. The reversible adhesive layer may have an adhesive strength substantially equivalent to that of the non-reversible adhesive layer.

The adhesive strength of the reversible adhesive layer and the non-reversible adhesive layer may be determined by using an ASTM international standard testing method number ASTM F2258-05(2010), entitled "Standard Test Method for Strength Properties of Tissue Adhesives in Tension."

Examples of the Non-Reversible Adhesive Layer

The non-reversible adhesive layer may comprise the non-reversible adhesive. The non-reversible adhesive layer is free of the reversible adhesive. For example, the non-reversible adhesive layer may be formed by deposition of a formulation comprising the non-reversible adhesive on the frontal surface of the adhesive article.

The non-reversible adhesive may comprise a conventional adhesive such as a pressure-sensitive adhesive or a chemical compound used in manufacturing of such conventional adhesives.

Examples of conventional adhesives are polymers of pressure-sensitive adhesives such as acrylate and/or methacrylate polymers formed by polymerization of acrylate monomers. Examples of such acrylate monomers are acrylic acid, methyl acrylate, methyl methacrylate, ethylacrylate, ethyl methacrylate, propyl acrylate, propyl methacrylate, n-butyl acrylate, n-butyl methacrylate, n-pentyl acrylate, n-hexyl acrylate, n-hexyl methacrylate, n-heptyl acrylate, n-octyl acrylate, n-nonyl acrylate, lauryl acrylate, stearyl acrylate, stearyl methacrylate, behenyl acrylate, octadecylacrylate, 2-ethylhexyl acrylate and mixtures thereof.

The non-reversible adhesive layer does not have the reversibility of the reversible adhesive layer disclosed above. Thus, the non-reversible adhesive layer may not comprise a reversible adhesive, a reversible polymer or a reversible monomer. For example, the non-reversible adhesive layer may not be thermally reversible. For example, when the temperature of the adhesive article is cooled below 37° C., the non-reversible adhesive layer may have substantially higher adhesive strength than the reversible adhesive layer.

The non-reversible adhesive layer may have any thickness, but the thickness is at least equal to or thicker than that of the chemical compound forming the layer. For example, if the layer comprises an 2-ethylhexyl acrylate monomer, its thickness may be equal to or thicker than that of this monomer. Sizes of dimers, trimers, oligomers or polymers of varying molecular weight of such monomers may also form the thickness of the non-reversible adhesive layer.

If the non-reversible adhesive layer is thinner than a predetermined thickness, the non-reversible adhesive layer may not have desired properties. For example, if the thickness of the layer deposited by using a non-reversible monomer is too thin, the non-reversible adhesive layer may not have sufficient adhesiveness. In another example, if the thickness of the layer deposited by using a pressure-sensitive monomer is too thin, the non-reversible adhesive layer may not have sufficient adhesive strength.

The predetermined thickness range depends on the chemical or physical properties of the chemical compound forming the non-reversible adhesive layer and its value may vary accordingly. This thickness may experimentally be determined for the non-reversible adhesive layer.

Examples of the Backing Material

The adhesive article may further comprise a backing material. These backing materials may have a variety of shapes and structures. For example the backing material may be substantially flat with relatively smooth surfaces, like polymer films; it may have a sponge-like structure; and it may also have surfaces comprising filamentary structures.

Examples of backing materials may be cloths, meshes, films and mixtures thereof. Examples of cloths may be woven cloths such as gauze, non-woven cloths, fabrics, sponges and composites thereof. Examples of films may include films manufactured by using polymers such as polyurethane, silicone, polyimide, poly(monochloro-p-xylylene) (e.g., parylene C), poly(dimethylsiloxane) (e.g., PDMS) or films manufactured by using biologically derived materials such as elastin, alginates, chitin, collagen and fibrin. Semi-permeable films may be used. Polypeptides derived from biologic materials such as elastin may also be used. Composites of all such materials may also be used to manufacture the backing materials.

Gauze, non-woven cloths, fabrics and/or the like can be manufactured by using fibers such as natural fibers, synthetic fibers and composites thereof. These fibers may comprise, for example, cotton, linen, jute, hemp, cotton, wool, wood pulp, regenerated cellulosic fibers such as viscose rayon and cuprammonium rayon, modified cellulosic fibers such as cellulose acetate, synthetic fibers such as those derived from polyesters, polyamides, polyacrylics, biocompatible/biodegradable fibers such as polylactone or composites thereof. Examples of such backing materials may further include polyester (Mylar or perforated Telfa films), polyurethane, silicone sheet, polypropylene (PP), polyethylene (PE), polyvinyl chloride (PVC) and composites thereof.

Examples of the Dressing Material

The adhesive article may further comprise a dressing material. Some examples of the dressing material are gauze, non-woven cloths, fabrics and the like. Other examples of the dressing material are hydrocolloids, hydrogels and alginates. Polyurethane and/or silicone foams may also be used as the dressing materials. Antimicrobial dressing materials are further examples of the dressing materials. Such dressing materials may comprise antimicrobial agents such as silver, in ionic or nanocrystalline form. Further examples of the dressing material are disclosed in a publication Jones et al. "ABC of Wound Healing. Wound Dressings," BMJ, pages 777-780, volume 332, Apr. 1, 2006. The entire content of this publication is incorporated herein by reference.

Exemplary Applications of the Adhesive Articles

The adhesive article may be used for variety of applications. For example, they may be used for medical applications. Examples of medical applications are surgical barriers, surgical patches (e.g., dural patches), surgical wraps (e.g., vascular, perivascular, adventitial, periadventitial wraps and adventitial sheets), surgical dressings, meshes (e.g., perivascular meshes), bandages, tapes, tissue coverings and the like. Other examples are medical dressings used to treat burned skin, covers for ostomies, adhesive articles used to hold medical devices such as catheters, tubes, electrocardiogram electrodes in place, covers for pressure ulcers and the like.

Although the adhesive article is described above by way of medical applications, it may be suitable for applications in other fields. For example, this adhesive article may be used for repair, replacement, repositioning or attachment of electronic, optical, electro-optical components or even automotive components.

Any combination of embodiments or examples disclosed above that comprise the reversible adhesive and the non-reversible adhesive may be suitable to form the adhesive article of this disclosure.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification, including in the scope which follow, are approximate, not exact. They are intended to have a reasonable range which is consistent with the functions to which they relate and with what is customary in the art to which they pertain.

We claim:

1. An adhesive article comprising:
at least one reversible adhesive layer that substantially reduces its adhesion when subjected to a change in temperature,
at least one non-reversible adhesive layer that does not substantially reduce its adhesion when subjected to a change in temperature, and
at least one backing material,
wherein the at least one backing material comprises at least one frontal surface to which the reversible and the non-reversible adhesive layers are attached,
wherein the at least one non-reversible adhesive layer surrounds the at least one reversible adhesive layer, and
wherein both the at least one reversible adhesive layer and the at least one non-reversible adhesive layer each has a surface that adheres to a surface of a material when the adhesive article is brought in contact with the material surface.

2. The adhesive article of claim 1, wherein the at least one reversible adhesive layer covers at least 0.1 percent surface area of the at least one frontal surface of the backing material.

3. The adhesive article of claim 2, wherein the at least one non-reversible adhesive layer covers at least 0.1 percent surface area of the at least one frontal surface of the backing material.

4. The adhesive article of claim 3, wherein the at least one reversible adhesive layer is not in contact with the at least one non-reversible adhesive layer.

5. The adhesive article of claim 3, wherein the at least one reversible adhesive layer is in contact with the at least one non-reversible adhesive layer.

6. The adhesive article of claim 5, wherein the at least one reversible adhesive layer and the at least one non-reversible layer overlap such that the at least one reversible adhesive layer partially covers the at least one non-reversible adhesive layer, or the at least one non-reversible adhesive layer partially covers the at least one reversible layer.

7. The adhesive article of claim 6, wherein the at least one reversible adhesive layer covers part of the at least one non-reversible adhesive layer.

8. The adhesive article of claim 6, wherein the at least one non-reversible adhesive layer covers part of the at least one reversible adhesive layer.

9. The adhesive article of claim 1, wherein the at least one reversible adhesive layer has adhesive strength higher than that of the at least one non-reversible adhesive layer.

10. The adhesive article of claim 1, wherein the at least one reversible adhesive layer has adhesive strength lower than that of the at least one non-reversible adhesive layer.

11. The adhesive article of claim 1, wherein the non-reversible adhesive layer completely surrounds the reversible adhesive layer.

12. The adhesive article of claim 1, wherein the non-reversible adhesive layer does not completely surround the reversible adhesive layer.

* * * * *

UNITED STATES PATENT AND TRADEMARK OFFICE
CERTIFICATE OF CORRECTION

PATENT NO. : 10,098,790 B2
APPLICATION NO. : 14/443332
DATED : October 16, 2018
INVENTOR(S) : Cesar Blanco et al.

It is certified that error appears in the above-identified patent and that said Letters Patent is hereby corrected as shown below:

On the Title Page

Item (73), should read:
-- ALFRED E. MANN INSTITUTE FOR BIOMEDICAL ENGINEERING AT THE UNIVERSITY OF SOUTHERN CALIFORNIA --

Signed and Sealed this
Twenty-fifth Day of February, 2020

Andrei Iancu
*Director of the United States Patent and Trademark Office*